United States Patent [19]

Johnson

[11] 4,346,070

[45] Aug. 24, 1982

[54] TEST FOR TERATOGENIC POTENTIAL EMPLOYING HYDRA

[75] Inventor: E. Marshall Johnson, Philadelphia, Pa.

[73] Assignee: Thomas Jefferson University, Philadelphia, Pa.

[21] Appl. No.: 139,269

[22] Filed: Apr. 11, 1980

[51] Int. Cl.³ .......................... A61K 49/00; C12Q 1/00
[52] U.S. Cl. .......................................... 424/9; 435/29
[58] Field of Search ............................. 424/9; 435/29

[56] References Cited

PUBLICATIONS

"Screening for Teratogenic Hazards: Nature of the Problems", E. Marshall Johnson, Ann. Rev. Pharmacol. Toxicol., 1981, 21:417-429.
"Screening for Teratogenic Potential: Are We Asking the Proper Question?", E. Marshall Johnson, Teratology 21:259 (1980).
"A Subvertebrate System for Rapid Determination of Potential Teratogenic Hazards," E. Marshall Johnson, Journal of Environmental Pathology and Toxicology 4:153-156 (1980).
"Practical Application of Systems for Rapid Detection of Potential Teratogenic Hazards", E. Marshall Johnson, In Press–Advances of Modern Toxicology, vol. 2.
Johnson, Am. Asso. Anatomists, Abstract of Papers reprint from The Anatomical Record, vol. 196, No. 3, Mar. 1980, p. 89A.
Loomis, J. Exp. Zool., vol. 132, 1956, pp. 555-573.
Gierer, Nature, New Biol., vol. 239, Sep. 27, 1972, pp. 98-105.
Wakeford, J. Embryol. Exp. Morph., vol. 54, 1979, pp. 171-183.
Lee, Biol. Bull., vol. 157, Oct. 1979, pp. 288-296.
Sugiyama, Develop. Growth & Differ., vol. 21, 1979, pp. 361-375.
Epp, Trans. Amer. Micros. Soc., vol. 98, No. 3, Jul. 1979, pp. 392-400.
Berking, J. Cell. Sci., vol. 40, 1979, pp. 193-205.
Webster, J. Embryol. Exp. Morph., vol. 27, No. 2, 1972, pp. 301-306.
Filskie, J. Cell. Sci., vol. 23, 1977, pp. 151-172.
David, Proc. Nat. Acad. Sci., (U.S.A.), vol. 75, Feb. 1978, pp. 886-890.
Yaross, J. Cell. Sci., vol. 34, 1978, pp. 1-26.
Gierer, Quart. Reviews of Biophy., vol. 10, 1977, pp. 529-593.
Berking, Wilhelm Roux's Arch., vol. 182, 1977, pp. 117-129.
Brode, J. Cell. Sci., vol. 20, 1976, pp. 29-46.
Schaller, Cell Differentiation, vol. 5, 1976, pp. 1-11, 13-20.
Lentz, J. Exp. Zool., vol. 159, 1965, pp. 181-194.
Burnett, (Ed.) Biol. of Hydra, 1973, pp. 255-267 (Acd. Press).
David, J. Cell. Sci., vol. 11, 1972, pp. 557-568.
Otto, J. of Exp. Zool., reprint, vol. 200, Jun. 1977, pp. 417-428.
Bode, Wilhelm Roux' Arch., vol. 171, 1973, pp. 269-285.
Wilson, Environmental Sci., Environment & Birth Defects, Acd. Press, N.Y., 1973, pp. 23-26.
Solomon, Developmental Biol., vol. 9, No. 3, Jun. 1964, pp. 315-326.
Ceron, J. Embryol. Exp. Morph., vol. 26, 1971, pp. 323-338.
Johnson, Organ & Tissue Spec. of Response to Teratogenic Insult, pub. in Neubert & Merker (Ed.), New Approaches to the Evaluation of Abnormal Embryonic Development, 2nd Sym. on Prenatal Develop., Sep. 1975, pub. Georg Thieme, Stuttgart, 1975, pp. 573-590.
Lenicque, Chem. Abs., vol. 67, 1967, Ab. No. 20417c.
Webster's 3rd New Int. Dict., unabridged, G&C Merriam Co., Springfield MA, 1963, pp. 438, 1110, 1421.
Edgar, Sci., vol. 198, Dec. 23, 1977, pp. 1285-1286.
Wilson, J. Environ. Path. & Toxicol., vol. 2, 1978, pp. 149-167.
Lenicque, Chem. Abs., vol. 69, 1968, Ab. No. 33770d.
Lenicque, Chem. Abs., vol. 76, 1972, Ab. No. 68712h.

Primary Examiner—Anna P. Fagelson
Attorney, Agent, or Firm—Woodcock, Washburn, Kurtz, Mackiewicz & Norris

[57] ABSTRACT

A novel method for determining the teratogenic potential of an agent of unknown teratogenic effect is described. This novel method comprises the steps of providing a plurality of artificial embryos, chronically exposing the embryos to varying concentrations of test agents, observing the exposed embryos over time to estimate a minimum teratogenic concentration of the test agent required to interfere with the development of the embryo, and comparing the minimum teratogenic concentration to a minimum adult reference concentration of the test agent which is toxic to normal adults. In this manner, the teratogenic potential of the test compound is indicated by the degree of difference between the teratogenic and adult reference concentrations.

7 Claims, No Drawings

TEST FOR TERATOGENIC POTENTIAL EMPLOYING HYDRA

CROSS REFERENCE TO RELATED APPLICATIONS

The present application is related to my prior copending application Ser. No. 119,658, filed Feb. 8, 1980, entitled "Method and Apparatus for Growing Hydrozoa," which is hereby incorporated by reference as if fully set forth herein.

BACKGROUND OF THE INVENTION

The present invention relates to methods of determining teratogenic potentials of compounds of unknown teratogenic effects. More particularly, the present invention relates to the field of determining such teratogenic potentials without testing these compounds in mammalian species. In particular, the present invention relates to the field of screening tests for predicting the teratogenic effects of compounds on developing systems so as to estimate their potential for producing adverse effects on human embryos.

In recent years, there has developed an increasing interest in preclinically evaluating drugs and food additives to determine their teratogenic potential. In the near future, the Toxic Substances Control Act will become operative, and will result in guidelines for testing which will consist of the evaluation of several areas of toxicity. Typically, such evaluations will result in a tier system composed of increasingly costly and time consuming studies as one moves through a particular tier sequence. The lowest level of a tier ideally consists of a single or small group of comparatively inexpensive tests to reveal the most flagrant of the bad actors, i.e., those having the most adverse effects. A basic screen should give few if any false negatives, i.e., indicate that a chemical is not a hazard when it actually is. A chemical being evaluated would not necessarily be examined in higher level tests if no adverse effects are evident in the initial screen for that particular toxic effect. If the initial screen were such that it gives a few false positives, it would still be of value in a tier system of safety evaluations. A substance initially indicated as a bad actor by the initial screen can clear its "reputation" at a higher level in the tier system by indicating that the evaluation by the screen was a false positive. A tier system of evaluation is a realistic and pragmatic approach to the problem of regulating environmental chemicals.

It is estimated that 50,000 to 70,000 different chemicals are already in the marketplace and that 200 to 400 new chemicals are produced each year. The tire system approach is an attempt to protect the population from adverse effects by permitting a large number of substances to be tested while keeping costs low enough not to hinder research and development by chemical and industrial manufacturers.

At the present time, the one tier system which lacks any kind of basic, initial screen is that for teratology. No rapid and inexpensive screening system of teratogenic potential has yet been disclosed. A manufacturer can thus establish that a particular chemical does not adversely affect embryonic development only by performing intermediate or higher level tier system studies for teratogensis and embryo-lethal effects. In order to serve forthcoming needs in such a manner, great numbers of trained people will be required. In the absence of substantial resource allocation, screening for teratogenic potential may lag behind other safety evaluations.

A developmental test applicable as a screen of environmental agents must detect agents to which the conceptus is uniquely susceptible. D. Karnofsky first stated the concept now established as Karnofsky's Law that "virtually" any substance is capable of adversely affecting the conceptus if given at a high enough dose level. In determining whether a particular chemical substance needs to be regulated on the basis of being of a developmental hazard, it is important to determine if the embryo is uniquely susceptible to the agent. Agents which are coaffective teratogens (adversely affecting the embryo but only at a dose level near that adversely affecting the adult) would not necessarily be regulated as a developmental hazard. In this instance, the regulatory level could be established on the basis of its toxicity to the adult. Inclusion of a safety factor would provide protection to the conceptus from a coaffective teratogen. Only non-coaffective teratogens (those adversely affecting the embryo at a level markedly below the dose needed to adversely affect the adult) would require regulation below that level affecting the adult.

According to current screening techniques, rats are the preferred species for determining the teratogenic potential of a suspected agent. At the present time, it is necessary to use several hundred rats (a majority of them pregnant), over about three months time and $50,000 to make a determination of the dose level producing adult toxicity and the dose level adversely affecting embryonic development.

One species which has been intensely investigated is the fresh water coelenterate *Hydra attenuata*. This species is readily grown in the laboratory and has been a favorate of developmental biologists, having been the subject of over 2,000 papers published since 1744. Of the many species of Hydra, *H. attenuata* is most ammenable to the studies in the laboratory as it is not complicated by associated organisms, such as algae. Since the usual method (Loomis and Lenhoff, '56) of growing *H. attenuata* is quite time consuming, a semi-automated system for their growth has been developed which is the topic of my co-pending patent application entitled "Method and Apparatus for Growing Hydrozoa," Ser. No. 119,658, filed Feb. 8, 1980.

Many methods are known for collecting and dissociating *H. attenuata* into their component cells. These methods date back over 100 years, however, the method developed by Gierer et al., "Regeneration of Hydra from Reaggregated Cells," *Nature New Biology*, 239: 98–105 (1972) is presently preferred. The dissociated cells are randomly packed by centrifugation and expelled into culture medium as pellets. Over the next 24 hours the medium is reduced in molarity until that necessary for adults is attained. The randomly associated cells of a pellet rapidly develop into two tissue layers with endodermal cells internally positioned, ectodermal cells externally positioned, and multipotent interstitial cells which differentiate into nematoblasts and nerve cells interspersed between them. (See, David and MacWilliams, "Regulation of the Self-Renewal Probability in Hydra Stem Cell Clones," *Proc. Natl. Acad. Sci. U.S.A.*, 75: 886–890, (1977) and Yaross and Bode, "Regulation of Interstitial Cell Differentiation in *Hydra attenuata*," *J. Cell Sci.* 34: 1–26, (1978)). A pellet of 50,000 or more cells (Gierer et al., "Regeneration of Hydra from Reaggregated Cells," *Nature New Biology*, 239:

98-105 (1972)) is needed to achieve 100% of the pellets surviving to form multi-attached *attenuata* which separate from one another becoming free standing and feeding adult animals within seven days.

In order for new adults to be formed the cells must achieve; survival, changes in cell size and shape (Gierer et al., "Physical Aspects of Tissue Evagination and Biological Form," *Quarterly Reviews of Biophysics,* 10: 529-593 (1977), and Webster and Hamilton, "Budding in Hydra: The Role of Cell Multiplication and Cell Movement in Bud Initiation," *J. Embryol. Exp. Morph.,* 27: 301-316 (1972)), selective cell death (Gierer et al., "Regeneration of Hydra from Reaggregated Cells," *Nature New Biology,* 239: 98-105, (1972)), cells must become spatially oriented, must recognize neighbors and form specialized junctions (Filskie and Flower, "Junctional Structures in Hydra," *J. Cell Sci.,* 23: 151-172, (1977) and Wakeford, "Cell Contact and Positional Communication in Hydra," *J. Embryol. Exp. Morph.,* 54: 171-183, (1979)), form selective adhesive associations and migrate, (Webster and Hamiston, "Budding in Hydra: The Role of Cell Multiplication and Cell Movement in Bud Initiation," *J. Embryol. Exp. Morph.,* 27: 301-316, (1972)), induce differentiation of other cells less differentiated than themselves (Browne, "The Production of New Hydranths in Hydra by the Insertion of Small Grafts," *J. Exp. Zool.,* (1909); Lee and Campbell, "Development and Behavior of an Integeneric Chimera of Hydra (Pelmathohydra Oligactis Interstitial Cells: *Hydra attenuata* Epithelial Cells)," *Biol. Bull.,* 157: 288-296, (1979); and Sugiyama and Fujisawa, "Genetic Analysis and Developmental Mechanisms in Hydra VII. Statistical Analysis of Developmental Morphological Characters and Cellular Compositions," *Develop.,* 1 Growth and Differ., 21: 361-375, (1979)), form intercellular matrix (Epp et al., "Isolation and Observation of Tissue Layers in *Hydra attenuata* Pall (Cnidaria, Hydrozoa)," *Trans. Amer. Micros. Soc.,* 98: 392-400, (1979)), be responsive to inductive stimuli and differentiate (Berking, "Control of Nerve Cell Formation from Multipotent Stem Cells in Hydra," *J. Cell Sci.,* 40: 193-205, (1979); Berking and Gierer, "Analysis of Early Stages of Budding in Hydra by Means of an Endogenous Inhibitor," *Wilhelm Roux's Archives,* 182: 117-129, (1977); Bode et al., "Regulation of Interstitial Cell Differentiation in *Hydra attenuata,*" *J. Cell Sci.,* 20: 29-46 (1976); Browne, "The Production of New Hydranths in Hydra by the Insertion of Small Grafts," *J. Exp. Zool.,* 7: 1-24, (1909); Schaller, "Action of the Head Activator as a Growth Hormone in Hydra," *Cell Differentiation,* 5: 1-11, (1976a); and Schaller, "Action of the Head Activator on the Determination of Interstitial Cells in Hydra," *Cell Differentiation,* 5: 13-20, (1976b)), form cell-specific organelles and products (Lentz, "Fine Structural Changes in the Nervous System of the Regenerating Hydra," *J. Exp. Zool.,* 159: 181-194, (1965)), undergo mitotic division and then differentiate (Burnett et al., "Regeneration of a Complete Hydra from a Single, Differentiated Somatic Cell Type" (Chapter 11) in *Biology of Hydra,* Ed. by: A. L. Burnett, Academic Press, (1973); and David and Campbell, "Cell Cycle Kinetics and Development of *Hydra attenuata,*" *J. Cell Sci.,* 11: 557-568, (1972)), form organ fields (Browne, "The Production of New Hydranths in Hydra by the Insertion of Small Grafts," *J. Exp. Zool.,* 7: 1-24, (1909); Gierer et al., "Physical aspects of Tissue Evagination and Biological Form," *Quarterly Reviews of Biophysics,* 10: 529-593, (1977); and Otto and Campbell, "Budding in *Hydra attenuata:* Bud Stages and Fate Map," *J. Exp. Zoology,* 200: 417-427, (1977)), and regulate organ field size (Bode et al., "Quantitative Analysis of Cell Types During Growth and Morphogenesis in Hydra," *Wilhelm Roux' Archiv.,* 171: 269-285, (1973) and Webster and Hamilton, "Budding in Hydra: The Role of Cell Multiplication and Cell Movement in Bud Initiation," *J. Embryol. Exp. Morph.,* 27: 301-316, (1972)), and become associated into tissues (Davis, "Histological and Ultrastructural Studies of the Basal Disk of Hydra III. The Gastrodermis and The Mesoglea," *Cell Tiss. Res.,* 162: 107-118, (1975)) capable of functioning as parts of an integrated, coordinated adult. This is essentially the same list of phenomena required of a zygote in becoming an embryo and then a fetus. It also encompasses all of the phenomena considered vulnerable to abnormality during the pathogenesis of a developmental abnormality (Wilson, *Environment and Birth Defects,* Academic Press, New York, p. 25, (1973)). It is not being implied that these phenomena are all the same as in higher forms. Perhaps the molecular mechanisms to achieve them however are more similar than different. The only basis for this rather interesting (though highly speculative) thought is that an agent held to disrupt microtubules (vinblastine) interferes with a reaggregate's activities during the time of most active cell migration and shape changing while an agent perturbing DNA synthesis (methotrexate) disrupts regeneration at the time of greatest cell multiplication.

These cell aggregations may be considered artificial "embryos" because the actual pellet stage only lasts half a day, by which time they become hollow, bilaminar spheres. By two days, tentacle buds are present which develop into tentacles by the end of day three. Hypostomal anlagen are present on day four, and by five days axises are present. The organisms then detach as independent small adults within one week. As used hereinafter, the term "embryo" will be used to include the entire time course and sequence of events ranging from the pellet form, through the development of tissues, into detached, independent small adults.

*Hydra attenuata* is not the only species to have been subjected to intensive research concerning its developmental characteristics. In particular, cellular slime molds, *Dictyostelium discoideum* and plants have received some attention as systems which may permit the prediction of teratogenic potential. See for example Solomon, E. P., E. M. Johnson and J. H. Gregg, (1964) "Multiple Forms of Enzymes in a Cellular Slime Mold During Morphogensis," *Developmental Biology,* Vol. 9, pp. 314-326. See also, Cereon, G. and E. M. Johnson, (1971) "Control of Protein Synthesis During the Development of Acetabularia," *J. Embyol. Exp. Morph.,* 26: 323-338; and Johnson, E. M., (1975) "Organ and Tissue Specificity in Response to Teratogenic Insult," appearing in *New Approaches to the Evaluation of Abnormal Embryonic Development,* edited by D. Newbert and H. J. Merker, Georg Thiem Publishers, pp. 573-590. It has also been suggested to use chicken eggs, Xenopus, and various sponges as systems for the screening of substances to determine their teratogenic potential. These systems have not gained wide spread acceptance, because of their cost, lack of reliability, limited response potential, or other factors interferring with simple, reliable testing.

SUMMARY OF THE INVENTION

The present invention relates to a process which will allow drugs, products, wastes or chemicals to be evaluated for their potential hazard of producing birth defects in mammals, including man.

The screening method of the present invention provides a plurality of artificial "embryos" which are exposed to test materials (i.e., agents) in preselected concentrations. In accordance with this method, adult animals are similarly exposed to these test materials in concentrations which are selected to produce adult toxicity within given lengths of time. Observations of both the artificial "embryos" and corresponding adult animals are made over time to determine the concentration of test agent and time required to interfere with the development of the artificial "embryo" and to determine the concentration of test agent necessary to produce adult toxicity within that length of time. According to the disclosed method, the determined concentrations (doses) of the test agents for a given period of exposure are then compared to determine how the concentration required to interfere with the development of the artificial "embryo" compares on the log scale to the concentration required to achieve an adult toxic response. It has been found that when the test agents are "non-teratogens" values which are considerably less than one log dose difference between the "embryo" and adult will be found, whereas for known teratogens, values of greater than one log dose will be determined. Thus, for an agent of unknown teratogenic potential, values of greater than one log dose identify the test agent as being a suspected teratogen uniquely hazardous to the conceptus.

The preferred genus for use in accordance with the method of the present invention is Hydra, a fresh water coelenterate. The species *Hydra attenuata* is particularly well suited for use in the preferred method of the present invention. According to the present method, Hydra are grown in a fluid medium in accordance with the method disclosed by Loomis and Lenhoff (1956) and fed *Artemia nauplii* each day. Adult Hydra are collected each day and dissociated into their individual component cells, and small cellular aggregates. The technique of Gierer et al., "Regeneration of Hydra from Reaggregated Cells," *Nature New Biology*, 239: 98–105, (1972) is suitable for use as this dissociation step. It is widely known that such dissociated cells will reaggregate through a sequence of stages in either dense culture or when packed by gentle centrifugation to reform adult Hydra within about a week.

Work has been conducted at Thomas Jefferson University which has exposed the reaggregating Hydra cells to known concentrations of agents having known effects on human and other mammalian embryos. Both drugs and chemicals have been studied, some of which are known to produce birth defects and others of which have been considered as lacking significant potential for adversely affecting embryonic development. Normal intact adult Hydra have similarly been exposed to the same drugs and chemicals at the same and higher preselected concentrations. In accordance with the preferred method of the present invention, a teratogenic potential value is determined by comparing the dose interferring with the reaggregation and the dose showing toxic effects on adults within the same number of hours or days. This information may be presented as a given value representing the log difference between concentrations, the ratio (or log thereof) of the adult/"embryo" affective dose or may be presented in dose response curves having as the variable either the duration of exposure or the test agent concentration. In each instance, the direct and primary effect of the test agent on both the reaggregate system and the adult individuals should be represented. Preferably, the object of the tests should be to determine the lowest concentration affecting the aggregates in the shortest period of time. Experimental results have indicated that some agents may show effects within 20 hours, while others require as much as six days.

The underlying theory of the present invention is that any agent is potentially capable of causing birth defects if the concentration of that agent is high enough. For example, doses producing overt maternal toxicity generally will affect reproduction adversely in mammals. It is the object of the present invention to distinguish between these agents and those which exhibit little or no adult toxicity but which have a unique and marked effect on a conceptus. The above described test utilizing Hydra has been shown to easily differentiate between doses adversely affecting the aggregate while not substantially affecting the adult. It has been found that agents known as potent teratogens (producers of birth defects) in animals and man have a dose differential of greater than one or two logs. Agents known as weak teratogens have a dose differential of about 1 log, whereas agents considered as "non" teratogens or as teratogens only in the presence of maternal toxicity have a dose differential of less than 0.30 log. Where data are available (e.g. NIOSH Registry of Toxic Effects of Chemical Substances) on effects in laboratory rodents (and humans) the Hydra system proves to be directly predictable of hazard to the mammalian conceptus. The only difference appears to be that this test takes only days and a few hundred dollars while tests in rodents take months and cost many thousand dollars.

PREFERRED EMBODIMENTS OF THE INVENTION

While the following description refers to specific examples, for the purpose of illustration, one of ordinary skill in the art will recognize that various alterations and modifications to the disclosed methods may be made without departing from the scope of the present invention, which is defined in the appended claims.

In accordance with the preferred method of the present invention, a plurality of artificial embryos are provided which are exposed to varying preselected concentrations of test compounds. Such artificial embryos, which are preferably the Hydra cell pellets, are grown in reaggregation media containing a test compound at log intervals of concentration from 0.01 through 10,000 $\mu$g/ml of medium. As soon as an adverse effect is seen, the lowest log dose achieving the effect is further subdivided either at quarter log doses or at 1/10 log doses in a second test run. The embryo time-to-effect is thus determined at the lowest affective dose and is considered to be the "embryo affective dose," or "minimum teratogenic concentration."

In accordance with the preferred embodiment, adult animals are similarly treated. The dose needed to adversely affect the adult in any way within the same number of hours as the embryo affective dose is considered as the adult affective dose. This gives a dose capable of interferring with the regenerating system and a dose toxic to the adult. In Table 1, various substances are listed which indicate the minimum embryo affective dose (minimum teratogenic concentration) and minimum adult affective dose (minimum adult reference concentration) for various test substances:

TABLE 1

| | (mg/l culture medium) | | |
|---|---|---|---|
| test substance | "embryo" affective dose | adult affective dose | time to effect (days) |
| aspirin | 375 | 500 | 3 |
| methotrexate | 50 | 175 | 7 |
| retinoic acetate | 7 | 15 | 2 |
| actinomycin D | 0.5 | 50 | 1 |
| vinblastine | 0.1 | 5 | 1 |
| isoniazid | 1 | 500 | 2 |
| dexamethasone | 90 | 200 | 2 |
| 6-AN | 10 | 625 | 3 |
| puromycin | 2.5 | 90 | 1 |

As seen from Table 1, the effects of drugs on regenerating *attenuata* cells in culture vary according to time. The irregular cell clump normally develops into a solid, smooth surfaced sphere by four hours. None of the drugs tested in Table 1 have interfered with this process. Between four and 24 hours, when the solid sphere develops into a hollow sphere, some of the tested drugs have been found to exert their effects. One sees the lack of, or only partial hollowing of the sphere followed by cell loss and disintegration. Often an aggregate will develop normally into a hollow sphere but will become arrested at this stage, disintegrating within the next eight hours. By 48 hours the aggregates should show initial development of tentacle buds which elongate with time. Some drugs allow the development of tentacle buds but inhibit their elongation. The cells on the surface of the aggregate then become clear and enlarge. This is followed by disintegration within the next 24 hours. Finally, a few drugs seem to exert their effects after 96 hours when the hypostome and body axis are forming. In this case, the aggregate continues to lose cells and disintegrates. In accordance with the preferred method of the present invention, the developing artificial embryos should be observed to identify the first observed of each of the above identified interferences.

As seen from Table 1, a wide variety of embryo versus adult affective dose differences are represented by the test substances. In accordance with the preferred embodiment of the present invention, the embryo affective dose (minimum teratogenic concentration) should be compared to the adult affective dose (minimum adult reference concentration), whereby the teratogenic potential of the given compound is indicated by the degree of difference between the teratogenic and adult reference concentrations.

In order to determine the degree of correspondence between results obtained using the above-described Hydra test, and the known effects of test substances on other species, such as rats, mice, and ultimately, man, the NIOSH Registry Lists have been used to locate information relating to the lowest published dose and route (and gestational days of treatment) producing a teratogenic effect. These Registry Lists also provide the lowest dose producing a lethal effect (LDLo) in adult animals. Unfortunately, the NIOSH Registry is in some instances incomplete, necessitating the substitution in the following table of the closest comparable route, source or species. Table 2 lists this Registry information for the test substances listed in Table 1.

TABLE 2

| | (mg/kg) | | | | | | | |
|---|---|---|---|---|---|---|---|---|
| | Teratogenic effect | | | | Adult effect parameter | | | |
| test substance | route | species | source | dose | dose | source | species | route |
| aspirin | ipr | rat | NIOSH (p.1134) | 250 | 420 | NIOSH, LDLo | rat | ipr |
| methotrexate | orl | human | NIOSH (p.604) | 0.625 (wk 8-10) | 2.5 | PDR, LDLo | human | orl |
| retinoic acetate | orl | mouse | NIOSH (p.1125) | 500 (day 9) | 1000 | NIOSH, LDLo | mouse | orl |
| actinomycin D | ipr | mouse | NIOSH (p.54) | 0.14 (day 6-8) | 0.67 | NIOSH LDLo | mouse | ivn |
| vinblastine | ims | rat | NIOSH (p.1297) | 0.25 (day 8) | 2.9 | NIOSH, LD50 | rat | ivn |
| isoniazid (non-acetylated) | orl | rat | NIOSH (p.685) | 14 (day 6-14) | 650 | NIOSH, LD50 | rat | orl |
| dexamethasome | scu | mouse | NIOSH (p.1008) | 26 (day 11-15) | 14 | NIOSH, LD50 | mouse | scu |
| 6-amino nicotinamide | ipr | rat | NIOSH (p.1072) | 5 (day 11) | 20 | NIOSH, LD50 | rat | ipr |
| | ipr | mouse | NIOSH (p.1072) | 9.5 (day 13) | 65 | NIOSH, LD50 | mouse | ipr |
| puromycin | ivn | rat | * | ca 0.14 | 335 | NIOSH LDLo (p.57) | mouse | ivn |

*Phone communication with J. G. Wilson who determined puromycin (unpublished) to be slightly less potent than actinomycin D.

Using the information from Tables 2 and 1, the degree of correspondence between the results obtained from the above-described Hydra screening test may be compared with known mammalian information concerning the teratogenic effect of the given test substances. This comparison is made by calculating the log dose of the ratio of the teratogenic to adult reference concentrations for mammals (as reported in the literature) and for *Hydra attenuata*, as reported in Table 1. This comparison of data shows a close correspondence between the teratogenic potentials determined for the test substances using either the above Hydra test, and the known information resulting from mammalian testing:

TABLE 3

| test substance | | log differences between adult and embryo affective doses | rank order of increasing uniqueness of developmental hazard beyond the adult toxic level | |
|---|---|---|---|---|
| | | | attenuata | mammals |
| aspirin | rat | 0.17 | 2 | 2 |
| | attenuata | 0.13 | | |
| methotrexate | human | 0.55 | | |
| | mouse | 0.69 | 4 | 5 |
| | attenuata | 0.58 | | (avg.0.62) |
| retinoic acetate | mouse | 0.5 | 3 | 3 |
| | attenuata | 0.35 | | |
| actinomycin D | mouse | 0.53 | 5 | 4 |
| | attenuata | 0.9 | | |
| vinblastine | rat | 0.94 | 6 | 7 |
| | attenuata | 1.3 | | |
| isoniazid (non-acetylated) | rat | 1.41 | 9 | 8 |
| | attenuata | 2.2 | | |
| dexamethasone | mouse | −0.21 (reversed doses) | 1 | 1 |
| | attenuata | 0.11 | | |
| 6-AN | rat | 0.6 | | |
| | mouse | 0.65 | 7 | 6 |
| | attenuata | 1.42 | | (avg.0.625) |
| puromycin | rat/-mouse | 2.9 (estimated) | 8 | 9 |
| | attenuata | 1.55 | | |

As seen from Table 3, the coaffective teratogens appear to be aspirin and dexamethasone. The non-coaffective teratogens are at least puromycin, 6-AN, isoniazid, and vinblastine. The other test substances listed in the tables are intermediate in developmental hazard potential. Although the affective dose levels in *attenuata* and mammals differs, the log differences between the affective doses are directly comparable and even provide a rank ordering which is precisely what the Interagency Testing Committee requires to establish priorities of need for detailed examination of potential environmental hazards.

Accordingly, the rank order achieved from the Hydra screen tests of the present invention is not only close to the order achieved from performing elaborate mammalian testing, but may be performed far more easily and at much less expense than the mammalian testing which would otherwise be required in order to produce such an index of teratogenic effect.

What is claimed is:

1. A method of determining the mammalian teratogenic potential of a compound (agent) of unknown mammalian teratogenic effect, comprising the steps of:
    (a) providing a plurality of artificial embryos of Hydra, said artificial embryos comprising Hydra cell pellets;
    (b) chronically exposing said embryos to varying preselected concentrations of said compounds;
    (c) observing said chronically exposed embryos over time to estimate a minimum teratogenic concentration of said compound required to interfere with the development of said embryo after a length of time;
    (d) comparing said minimum teratogenic concentration to a minimum adult reference concentration of said compound which is toxic to normal adult Hydra;
    whereby the mammalian teratogenic potential of said compound is indicated by the degree of difference between said teratogenic and adult reference concentrations.

2. The method of claim 1 wherein said step (d) further comprises the step of determining the log of a ratio of said concentrations to produce an index value corresponding to said teratogenic potential.

3. The method of claim 1 wherein step (a) further comprises preparing dissociated cells of Hydra for reaggregation by reassociating said cells into said pellets.

4. The method of claim 1 comprising the further step of chronically exposing adults to preselected concentrations of said compound.

5. The method of claim 4 wherein said method further comprises the step of observing said chronically exposed adults over time to estimate a minimum adult reference concentration of said compound which is toxic to said adults.

6. The method of claim 4 wherein said minimum teratogenic concentration is determined at the time interference with said development is first observed.

7. The method of claim 6 wherein said adult reference concentration is determined for a chronic exposure time which equals the time after which said interference with said development is first observed.

* * * * *